United States Patent [19]

Fujie et al.

[11] Patent Number: 4,748,336

[45] Date of Patent: May 31, 1988

[54] OPTICAL DUST DETECTOR ASSEMBLY FOR USE IN AN AUTOMOTIVE VEHICLE

[75] Inventors: Fumiaki Fujie, Oobu; Tetsuro Adachi, Okazaki; Tomonori Fukui, Kariya; Noboru Oyama, Okazaki; Yukiyasu Ueno, Kariya, all of Japan

[73] Assignee: Nippondenso Co., Ltd., Kariya, Japan

[21] Appl. No.: 858,168

[22] Filed: May 1, 1986

[30] Foreign Application Priority Data

May 1, 1985 [JP] Japan ................................. 60-94765
Sep. 2, 1985 [JP] Japan ................................. 60-193324

[51] Int. Cl.$^4$ ...................... G01N 15/06; G01N 21/00
[52] U.S. Cl. ..................................... 250/573; 356/439
[58] Field of Search ............... 250/239, 573, 574, 575; 340/603, 628, 630; 356/335, 336, 438, 439

[56] References Cited

U.S. PATENT DOCUMENTS

| 3,313,946 | 4/1967 | Goodwin et al. | 340/630 |
| 3,659,278 | 4/1972 | Jensen | 340/630 |
| 3,816,004 | 6/1974 | Bignardi | 250/573 |
| 3,946,234 | 4/1976 | Vandermark | 340/630 |
| 4,662,758 | 5/1987 | Fukui et al. | 356/439 |

FOREIGN PATENT DOCUMENTS 679904  8/1979  U.S.S.R. .

Primary Examiner—David C. Nelms
Assistant Examiner—Stephone B. Allen
Attorney, Agent, or Firm—Cushman, Darby & Cushman

[57] ABSTRACT

An optical dust detector assembly includes an air duct member having an introductory portion and a base portion for permitting a flow of air passing therethrough, the duct member having a pair of radial holes formed in its peripheral wall, a pair of cylindrical casings secured to the peripheral wall of the duct member at both sides thereof and having respective opening ends communicating with the interior of the duct member through the respective radial holes thereof, a light emission element arranged within one of the casings to emit a light beam and pass it through the radial holes toward the other casing, and a light receiving element arranged within the other casing to receive the light beam emitted from the light emission element and passed through the radial holes. The air duct member is bent in such a manner as to form therein an inclined internal surface for deflecting upwardly the flow of air introduced through the introductory portion, and the radial holes are formed in a peripheral wall of the base portion of the duct member to face the flow of air deflected by the inclined internal surface so that foreign particles like rain or snow are not deflected upward toward the optical detector.

4 Claims, 3 Drawing Sheets

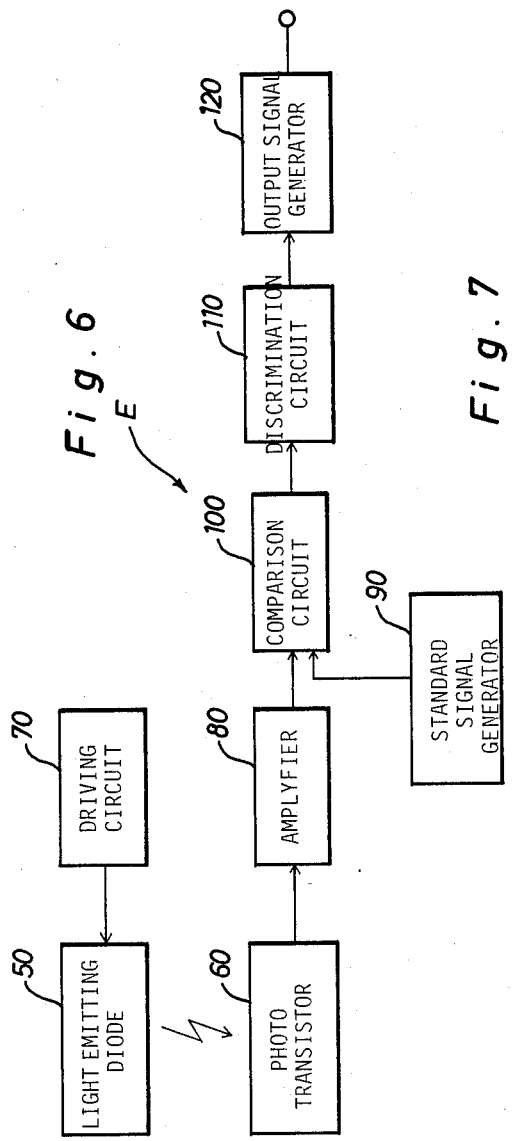
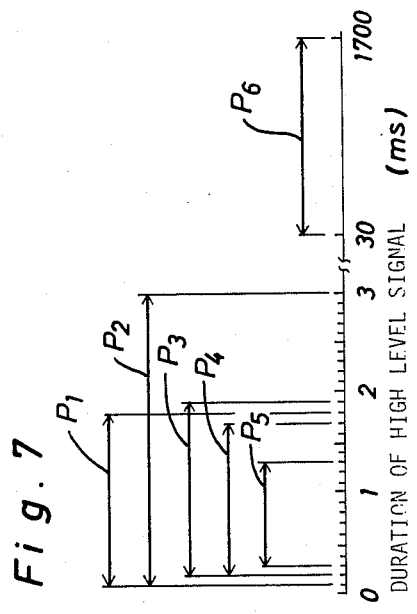

OPTICAL DUST DETECTOR ASSEMBLY FOR USE IN AN AUTOMOTIVE VEHICLE

BACKGROUND OF THE INVENTION

The present invention relates to an optical detector assembly, and more particularly to an optical dust detector assembly adapted for use in an automotive vehicle for detecting the concentration of dust, smoke or the like contained in a flow of air passing therethrough.

An optical dust detector assembly of this type includes a cylindrical air duct member having an introductory portion with an inlet opening, and a base portion with an outlet opening, for permitting dust-containing air to pass therethrough, the air duct member having a pair of radial holes formed in its peripheral wall and opposed to each other, a pair of cylindrical casings secured to the peripheral wall of the air duct member on both lateral sides thereof with respective opening ends communicating with the interior of the air duct member through the respective radial holes thereof, a light emission element arranged within one of the casings to emit a light beam therefrom and pass it through the radial holes toward the other casing, and a light receiving element arranged within the other casing to receive the light beam emitted from the light emission element and passed through the radial holes, the light receiving element detecting a decrease in the intensity of the received light beam caused in response to an increase of the dust concentration in the air introduced into the air duct member through the introductory portion thereof.

In such a conventional optical dust detector assembly as described above, depending on the position of the detector assembly in the vehicle, small foreign particles such as dirt, rain, snow, sleet or water splash may be present in the dust-containing air introduced through the introductory portion of the air duct member. This causes the intensity of the received light beam to be varied due to the presence of those foreign particles other than dust. In other words, the optical dust detector assembly will detect not only dust to be detected but also those foreign particles other than the dust, resulting in the occurrence of errors in dust detection. Furthermore, by adhesion of the foreign particles to the light emission element, light receiving element or other optical elements, the optical functions of the dust detector assembly may deteriorate.

SUMMARY OF THE INVENTION

It is, therefore, an object of the present invention to provide an improved optical detector assembly wherein, in view of the fact that dust particles are much smaller in both diameter and mass than the foreign particles such as dirt, rain, snow, sleet or water splash, the latter are separated from the flow of dust-containing air passing through the air duct member so as to prevent adhesion of the foreign particles to the optical elements of the detector assembly, and to enable reliable detection of the dust concentration in the flow of air.

According to the present invention, the object is accomplished by the provision of an optical dust detector assembly of the kind described above, wherein the air duct member is bent in such a manner as to form therein an inclined internal surface for deflecting the flow of air introduced through the introductory portion thereof, and wherein the radial holes are formed in a peripheral wall of the base portion of the duct member to face the flow of air deflected by the inclined internal surface. In the case that the optical dust detector assembly is arranged in a fore-and-aft direction on a vehicle body structure, it is preferable that the introductory portion of the duct member is bent in such a manner as to incline downwardly from the base portion toward the front of the vehicle so as to form an inclined internal surface for deflecting upwardly the flow of air introduced therein, wherein the radial holes are formed in a peripheral wall of the base portion of the duct member to face the flow air deflected upwardly by the inclined internal surface. Alternatively, the base portion of the duct member may be bent in such a manner as to incline upwardly from the introductory portion toward the rear of the vehicle so as to form an inclined internal surface for deflecting upwardly the flow of air introduced therein through the introductory portion, wherein the radial holes are formed in a peripheral wall of the base portion of the duct member to face the flow of air deflected upwardly by the inclined internal surface.

In a practical embodiment of the present invention, an electric control apparatus coupled to the dust detector assembly comprises a standard signal generator for producing a standard signal indicative of a predetermined concentration of dust, a comparator responsive to an output signal from the light receiving element and the standard signal from the standard signal generator to produce a high level signal therefrom when the output signal is maintained in a lower level than the standard signal level, a discrimination circuit responsive to the high level signal from the comparator to produce a detection signal therefrom only when the high level signal is maintained in a period of time more than a predetermined duration, and an output signal generator arranged to produce a control signal therefrom in response to the detection signal from the discrimination circuit.

BRIEF DESCRIPTION OF THE DRAWINGS

Additional objects and advantages of the present invention will become more readily apparent from the following detailed description of preferred embodiments thereof when taken together with the accompanying drawings, in which;

FIG. 6 illustrates a block diagram of an electric control apparatus coupled to the optical dust detector assembly shown in FIGS. 1 and 3; and FIG. 7 is a graph illustrating each duration of high level signals indicative of the concentration of rain, snow, sleet, water splash and dust.

DETAILED DESCRIPTION OF THE PREFERRED EMBODIMENTS

Figure 3:
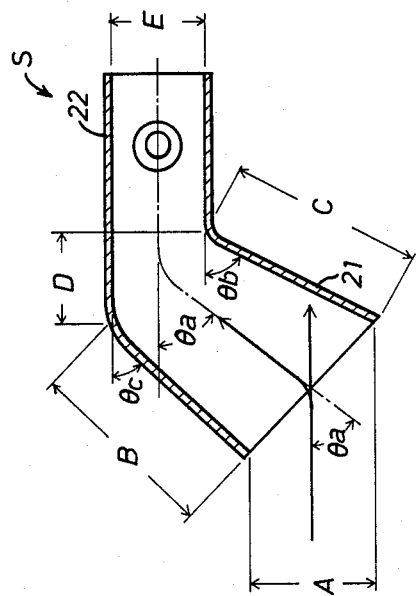
FIG. 3 is a cross-sectional side view taken along line III—III in FIG. 1.
Figure 1:
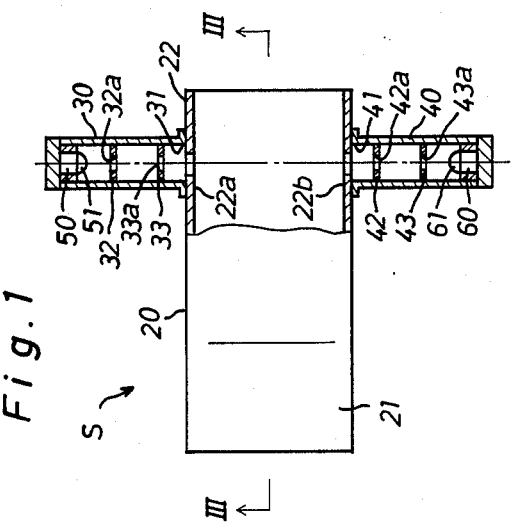
FIG. 1 is a fragmentary cross-sectional plan view of an optical dust detector assembly in accordance with the present invention.
Figure 2:
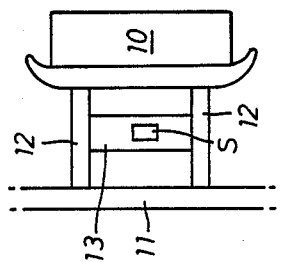
FIG. 2 illustrates an arrangement of the detector assembly of FIG. 1 on a vehicle body structure.

With reference to the drawings, FIGS. 1 through 3 show an optical dust detector assembly S of the light transmission type in accordance with the present invention, which is coupled to an electric control apparatus for an automobile air conditioner. As is illustrated in FIG. 2, the optical dust detector assembly S is fixedly mounted on the central portion of a lateral plate 13 the opposite ends of which are fixed to a pair of parallel chassis arms 12, 12 extending between a radiator 10 in front of a vehicle engine (not shown) and a front bumper 11 of the vehicle. As is illustrated in FIGS. 1 and 3, the optical dust detector assembly S includes a cylindrical air duct member 20, a pair of cylindrical casings 30, 40, a light emission element 50, and a light receiving element 60.

The air duct member 20 includes an introductory portion 21 and a base portion 22 and is fixedly mounted on the lateral plate 13 in a fore-and-aft direction of the vehicle. The introductory portion 21 has an inlet opening directed toward front bumper 11, being bent to incline downwardly from the base portion 22 toward the front of the vehicle. The base portion 22 is arranged in parallel to the surface of lateral plate 13 and has a pair of radial holes 22a and 22b formed in its peripheral wall and opposed to each other. The casing 30 is arranged in such a manner that the central axis thereof is perpendicular to the central axis of base portion 22 and has an opening end 31 fixed to the periphery of radial hole 22a. The casing 40 is arranged symmetrically to the casing 30 with respect to base portion 22 and has an opening end 41 fixed to the periphery of radial hole 22b. Here the central axes of both casings 30 and 40 coincide with each other.

The light emission element 50 is in the form of a light emitting diode which is fixedly mounted in place within the bottom portion of casing 30 with a light emission surface 51 thereof directed toward opening end 31 in such a manner that the axis of the light beam emitted from the light emission element 50 coincides with the central axis of casing 30. Provided within the casing 30 between light emission surface 51 and opening end 31 are a pair of laterally spaced partition plates 32 and 33, which are formed at their central portions with central holes 32a and 33a respectively, the centers of which central holes 32a and 33a are aligned with the axis of the emitted light beam and the inner diameters of which are smaller than that of radial hole 22a of base portion 22. The light beam emitted from light emission element 50 passes through the light emission surface 51 and the central holes 32a and 33a.

The light receiving element 60 is in the form of a photo transistor which is fixedly mounted in place within the bottom portion of casing 40 with a light receiving surface 61 thereof directed toward opening end 41 in such a manner that the axis of the light beam received by light receiving element 60 coincides with the central axis of casing 40. Provided within the casing 40 between light receiving surface 61 and opening end 41 are a pair of laterally spaced partition plates 42 and 43, which are formed at their central portions with central holes 42a and 43a respectively, the centers of which central holes 42a and 43a are aligned with the axis of the light beam to be received, and the inner diameters of which are smaller than that of radial hole 22b of base portion 22. The light receiving element 60 produces an electric output signal indicative of the intensity of the light beam which is emitted from light emission element 50, passes across the interior of base portion 22 of air duct member 20, and is received by light receiving surface 61.

In the arrangement of the optical dust detector assembly as described above, a series of dimensions and angles applied to the air duct member 20, being A–E and $\theta a$–$\theta c$ as designated in FIG. 3, are to be determined by taking the following criteria into consideration:

1. Since the size of dust particles, about 0.02–30 $\mu m$ in diameter, is smaller than that of foreign particles other than dust, such as dirt, rain, snow, sleet or water splash which are about 0.15 mm–3 mm in diameter, the mass of dust is much smaller than that of the foreign particles. As a result, when the vehicle is moving or stationary with the fan of radiator 10 running, if the flow of air is deflected upwardly, from being parallel to lateral plate 13, by conducting it through the upwardly inclined introductory portion 21 of air duct member 20, dust particles are readily drawn into the upward flow of air, while foreign particles flow straight on due to their larger inertia. This phenomenon is also influenced by the velocity range of the air flow.

2. In the case that the height A of the inlet opening of introductory portion 21, or the area of the inlet opening thereof, is properly determined, it is desirable to make the length B of the upper side of introductory portion 21 possibly longer for more effective separation of the foreign particles.

In operation, when the optical dust detector assembly S as described above is activated, the light beam emitted from light emission element 50 passes through central holes 32a, 33a in partition plates 32, 33, radial holes 22a, 22b in the peripheral wall of base portion 22, and central holes 42a, 43a in partition plates 42, 43. The light beam travels along the light emission axis and then along the light receiving axis and is received by the light receiving element 60, which produces an electric output signal indicative of the intensity of the light beam. When the vehicle is in motion, dust whose mass is as small as described above is readily carried along with the air flow from the inlet opening of introductory portion 21, through the base portion 22 of duct member 20 toward the rear of the vehicle in such a manner as to change its flow direction smoothly from horizontal to upwardly along the upwardly bent introductory portion 21, and then back again to horizontal along the base portion 22. As a result, the intensity of the light beam received by light receiving element 60 decreases in dependence upon an increase of the dust concentration in the air flow, causing a decrease in the value of the electric output signal. In this case, even when the dust-containing air enters into casings 30 and 40 through radial holes 22a and 22b respectively, the optical system including the light emission element 50 and light receiving element 60 is reliably protected from dust by the blocking action of central holes 32a, 33a, 42a, and 43a formed in respective partition plates 32, 33, 42 and 43, owing to their small diameters.

Foreign particles such as dirt, rain, snow, sleet, or water splash, which are carried by the air flow and enter into the air duct member 20 with the dust, flow straight on and are separated from the upwardly bent air flow due to their large size or large inertia in comparison with the dust. They collide with the lower inside surface of introductory portion 21 and fall therealong, thereby to be reliably prevented from entering into base portion 22. Thus, dust-containing air free from foreign particles flows into the base portion 22. As a result, the intensity of the light beam received by light receiving element 60 is not affected by the presence of the foreign particles, so that the light receiving element can produce accurately an electric output signal indicative of the dust concentration only in the air flow. Furthermore, reliable prevention of the foreign particles from entering into base portion 22 serves for effective protection of both light emission element 50 and light receiving element 60 from contamination by the foreign particles.

In a practical embodiment, an air duct member 20 whose dimensions and angles are determined as follows is capable of effecting reliable dust separation from foreign particles in order to obtain satisfactory experimental results when the speed of the vehicle is varied between 0 to 110 Km/h, corresponding to a speed of the air flow at the optical dust detector assembly S between 0–60 Km/h:

$\theta a = 40°–50°$, $\theta b = 45°$, $\theta c = 55°$, B=40 mm, C=40 mm, and D=5 mm.

Figure 4:
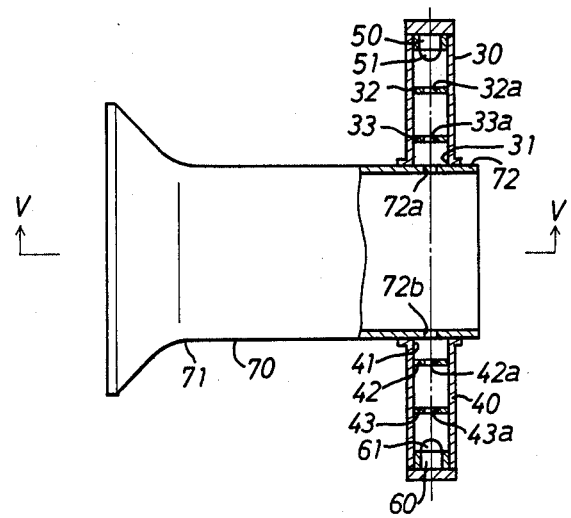
FIG. 4 is a fragmentary cross-sectional plan view of a modification of the present invention.
Figure 5:
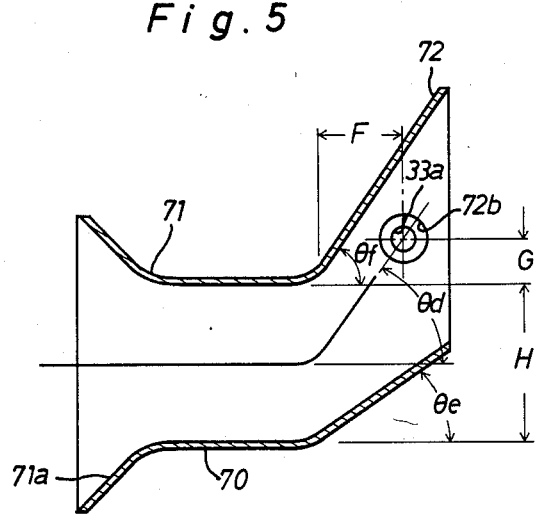
FIG. 5 is a cross-sectional side view taken along line V—V in FIG. 4.

Describing now a modification of the optical dust detector assembly in accordance with the present invention, as shown in FIGS. 4 and 5, a cylindrical air duct member 70 is employed in place of the air duct member 20 in the above-described embodiment. The air duct member 70 has an introductory portion 71 directed toward the front bumper 11, and a base portion 72, and is fixedly mounted on the lateral plate 13. The introductory portion 71 is arranged in parallel to the surface of lateral plate 13 and has an inlet opening 71a widened toward the front of the vehicle. The base portion 72 is bent in such a manner as to incline upwardly from the introductory portion 21 toward the rear of the vehicle and has a pair of radial holes 72a, 72b formed in its peripheral wall and opposed to each other. Fixed to the peripheries of radial holes 72a, 72b are a pair of casings 30, 40 with opening ends 31, 41 respectively to communicate with the interior of air duct member 70. A series of dimensions and angles applied to the air duct member 70, being F–H and $\theta d$–$\theta f$ as designated in FIG. 5, are to be determined by taking the criteria as described in the above embodiment into consideration. The remaining construction is substantially the same as that of the first-described embodiment.

In the operation of this modification, similarly to the first-described embodiment, foreign particles which are carried by the air flow and enter into the air duct member 70 with the dust flow straight on. They are separated from the upwardly bent air flow at the rear end of introductory portion 71 by colliding with the lower inside surface of base portion 72 and thus are prevented from entering into both radial holes 72a and 72b. As a result, the dust-containing air free from foreign particles flows through base portion 72 between radial holes 72a and 72b to achieve the same effects as those of the first-described embodiment. In a practical embodiment of this modification, an air duct member 70 whose dimensions and angles are determined as follows is capable of obtaining substantially the same satisfactory experimental results as those of the first-described embodiment:

$\theta d = 39°–47°$, $\theta e = 27°–37°$, $\theta f = 51°–56°$, F=13 mm–15 mm, G=7 mm–13 mm, and H=15 mm.

In FIG. 6, there is schematically illustrated a block diagram of an electric control apparatus coupled to the optical dust detector assembly shown in FIGS. 1 and 3. The electric control apparatus includes a driving circuit 70 connected to the light emitting diode 50, an amplifier 80 connected to the photo transistor 60, a standard signal generator 90, a comparison circuit 100 connected to the amplifier 80 and standard signal generator 90, a discrimination circuit 110 connected to the comparison circuit 100, and an output signal generator 120. The driving circuit 70 is connected to an electric power source in the form of a vehicle battery (not shown) through a user actuable switch to energize the light emitting diode 50 in its activated condition. The amplifier 80 is arranged to amplify an electric output signal indicative of the dust concentration applied thereto from the photo transistor 60 so as to produce an amplified signal therefrom. The standard signal generator 90 is arranged to produce a standard signal indicative of a predetermined concentration of the dust, dirt, rain, snow, sleet, water splash and the like contained in a flow of air introduced into the air duct member 20 of the detector assembly S. The comparison circuit 100 is responsive to the amplified signal from amplifier 80 and the standard signal from generator 90 to produce a high level signal therefrom when the amplified signal is maintained at a lower level than the standard signal level. The discrimination circuit 110 is responsive to the high level signal from comparison circuit 100 to produce a detection signal therefrom only when the high level signal is maintained in a period of time more than a predetermined duration. The output signal generator 120 is arranged to produce a control signal in response to the detection signal from discrimination circuit 110. In this embodiment, the predetermined duration for discrimination of the high level signal from comparison circuit 100 is determined to be 3 ms–30 ms for the following reason.

In an experiment, it has been observed that when the concentration of dust, rain, snow, sleet or water splash introduced into the air duct member 20 exceeds the predetermined value defined by the standard signal, the high level signal from comparison circuit 100 is maintained as shown in FIG. 7. The reference characters $P_1$–$P_6$ in FIG. 7 represent the facts that the high level signal indicative of the concentration of rain in a field is maintained in a period of 1.8 ms, that the high level signal indicative of the concentration of rain in a wind tunnel is maintained in a period of 3 ms, that the high level signal indicative of the concentration of snow is maintained in a period of 0.2 ms–1.9 ms, that the high level signal indicative of the concentration of sleet is maintained in a period of 0.2 ms–1.7 ms, that the high level signal indicative of the concentration of water splash is maintained in a period of 0.3 ms–1.3 ms, and that the high level signal indicative of the concentration of dust is maintained in a period of 30 ms–1700 ms.

In operation of the electric control apparatus, the level of an electric output signal of photo transistor 60 decreases in dependence upon an increase of the concentration of dust contained in a flow of air passing through the air duct member 20 of the dust detector assembly S. The output signal of photo transistor 60 is amplified by the amplifier 90 and applied to the comparison circuit 100. While the level of the amplified signal is maintained below the level of the standard signal from standard signal generator 90, the comparison circuit 100 produces a high level signal indicative of the concentration of dust. In such a condition, even if the high level signal of comparison circuit 100 is partly caused by presence of the foreign particles in the base portion 22 of air duct member 20, it will be maintained during a period of 30 ms–1700 ms more than the predetermined duration of 3 ms–30 ms. Thus, the discrimination circuit 110 produces a detection signal therefrom in response to the high level signal from comparison circuit 100, and in turn, the output signal generator 120 produces a contron signal therefrom in response to the detection signal from discrimination circuit 110. This enables reliable detection of the dust concentration in the flow of air passing through the air duct member 20 of the detector assembly S.

When any dust is not contained in the flow of air, the comparison circuit 100 does not produce any high level signal therefrom because the level of the amplfied signal from amplifier 80 is maintained above the standard signal level. If the level of the amplified signal from amplifier 80 drops below the standard signal level due to presence of foreign particles in the base portion 22 of air duct member 20, the high level signal of comparison circuit 100 will disappear within the predetermined duration of 3 ms–30 ms. In such a situation, the discrimination circuit 110 does not produce any detection signal therefrom to avoid errors in detection of the dust concentration in the flow of air.

In the above-described embodiments, the present invention is applied to an optical dust detector assembly of the light transmission type, but is applicable also to a detector assembly of the light scattering type.

Having now fully set forth both structure and operation of certain preferred embodiments of the concept underlying the present invention, various other embodiments as well as certain variations and modifications of the embodiments herein shown and described will obviously occur to those skilled in the art upon becoming familiar with said underlying concept. It is to be understood, therefore, that within the scope of the appended claims, the invention may be practiced otherwise than as specifically set forth herein.

What is claimed is:

1. An optical dust detector assembly adapted for use in an automotive vehicle for detecting the concentration of dust, smoke or the like contained in a flow of air passing therethrough, the detector assembly comprising:
    air duct means arranged parallel to said air flow and having an introductory portion with an inlet opening, a base portion with an outlet opening, and a pair of radial holes formed in a base portion in peripheral wall and opposed to each other;
    a pair of casings disposed at said base portion peripheral wall on both sides thereof and having respective openings ends communicating with the interior of said base portion through the respective radial holes thereof;
    a light emission element arranged within one of said casings to emit a light beam therefrom and pass it through the radial holes of said base portion toward the other casing; and
    a light receiving element arranged within the other casing to receive the light beam emitted from said light emission element and passed through the radial holes of said base portion;
    wherein said air duct member is bent in such a manner as to provide therein an inclined internal surface for deflecting upwardly the flow of air introduced through the introductory portion thereof, and wherein the radial holes are formed in the peripheral wall of the base portion of said duct member to face the flow of air after deflection by the inclined internal surface.

2. An optical dust detector assembly as claimed in claim 1, wherein said light receiving element is arranged to produce an electric output signal indicative of the concentration of duct contained in the flow of air passing through said air duct member, and wherein an electric control apparatus coupled to said light receiving element comprises a standard signal generator for producing a standard signal indicative of a predetermined concentration of dust, a comparator responsive to the output signal from said light receiving element and the standard signal from said standard signal generator to produce a high level signal therefrom when the output signal is maintained at a lower level than the standard signal level, a discrimination circuit responsive to the high level signal from said comparator to produce a detection signal therefrom only when the high level signal is maintained in a period of time more than a predetermined duration, and an output signal generator arranged to produce a control signal therefrom in response to the detection signal from said discrimination circuit.

3. An optical dust detector assembly according to claim 1, wherein said introductory portion of said duct member is bent in such a manner as to incline downwardly from said base portion toward a front of said vehicle so as to form said inclined internal surface for deflecting upwardly the flow of air introduced therein.

4. An optical dust detector assembly according to claim 1, wherein said base portion of said duct member is bent in such a manner as to incline upwardly from said introductory portion toward a rear of said vehicle so as to form said inclined internal surface for deflecting upwardly the flow of air introduced therein through said introductory portion.

* * * * *